United States Patent
Yada et al.

(10) Patent No.: US 7,319,162 B2
(45) Date of Patent: Jan. 15, 2008

(54) METHOD OF DECOMPOSING BY-PRODUCT DURING THE PRODUCTION OF (METH)ACRYLIC ESTER

(75) Inventors: Shuhei Yada, Mie (JP); Kenji Takasaki, Mie (JP); Yasushi Ogawa, Mie (JP); Yoshiro Suzuki, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 159 days.

(21) Appl. No.: 10/870,930

(22) Filed: Jun. 21, 2004

(65) Prior Publication Data

US 2004/0225149 A1 Nov. 11, 2004

Related U.S. Application Data

(63) Continuation of application No. PCT/JP02/12976, filed on Dec. 11, 2002.

(30) Foreign Application Priority Data

Dec. 26, 2001 (JP) ............................. 2001-394447

(51) Int. Cl.
*C07C 67/48* (2006.01)
(52) U.S. Cl. .................................................. 560/218
(58) Field of Classification Search ................ 560/205, 560/208, 217, 218
See application file for complete search history.

(56) References Cited

U.S. PATENT DOCUMENTS

| | | | | |
|---|---|---|---|---|
| 5,734,075 A | * | 3/1998 | Fauconet et al. | ........... 560/218 |
| 5,767,306 A | * | 6/1998 | Aichinger et al. | .......... 560/212 |
| 5,883,288 A | | 3/1999 | Iffland et al. | |
| 6,072,076 A | | 6/2000 | Schmidt et al. | |
| 6,482,976 B1 | * | 11/2002 | Ho et al. | ..................... 560/205 |
| 2001/0047106 A1 | | 11/2001 | Aichinger et al. | |

FOREIGN PATENT DOCUMENTS

| | | |
|---|---|---|
| CN | 1140162 A | 1/1997 |
| JP | 5-25086 A | 2/1993 |
| JP | 6-65149 A | 3/1994 |
| JP | 8-183756 A | 7/1996 |

* cited by examiner

*Primary Examiner*—Karl Puttlitz
(74) *Attorney, Agent, or Firm*—Oblon, Spivak, McClelland, Maier & Neustadt, P.C.

(57) ABSTRACT

A method of decomposing a Michael addition reaction product formed as a by-product in the production step of a(meth)acrylic ester and recovering (meth)acrylic acid, a (meth)acrylic ester and an alcohol, in which the formation of an olefin as a by-product can be suppressed. A method of thermally decomposing a by-product at the time of production of a (meth)acrylic ester using an alcohol bearing a branched chain and having 3 or more carbon atoms, wherein the decomposition reaction is carried out in the absence of a catalyst.

12 Claims, 1 Drawing Sheet

METHOD OF DECOMPOSING BY-PRODUCT DURING THE PRODUCTION OF (METH)ACRYLIC ESTER

This application is a continuation of international application PCT/JP02/12976, filed Dec. 11, 2002.

TECHNICAL FIELD

The present invention relates to a method of decomposing a by-product during the production of a (meth)acrylic ester by decomposing a by-product at the time of production of a (meth)acrylic ester using an alcohol bearing a branched chain and having 3 or more carbon atoms, thereby recovering (meth)acrylic acid, (meth)acrylic ester, alcohol, and the like.

Incidentally, in the present description, the (meth)acrylic acid is a generic name to acrylic acid and methacrylic acid and may refer to either one or both of them.

BACKGROUND ART

As is well known, there is a vapor phase oxidation method of propylene as the formation reaction of acrylic acid for producing an acrylic ester. In a method of obtaining acrylic acid by oxidizing propylene, since condition of the oxidation to acrolein and that of the subsequent oxidation to acrylic acid are different from each other, the method includes a two-stage process of conducting the oxidation in separate reactors and a process oxidation directly to acrylic acid by one-stage oxidation.

FIG. 1 shows one embodiment of a step flow of forming acrylic acid by two-stage oxidation and subsequently esterifying it to produce an acrylic ester, in which propylene, steam and air are subjected to two-stage oxidation through a first reactor and a second reactor each charged with a molybdenum based catalyst, etc. to form an acrylic acid-containing gas. The acrylic acid-containing gas is brought into contact with water in a condensing column to form an acrylic acid aqueous solution, to which is then added a suitable extraction solvent; the mixture is subjected to extraction in an extracting column; and the extraction solvent is then separated in a solvent separating column. Subsequently, acetic acid is separated in an acetic acid separating column to obtain crude acetic acid, and a by-product is separated from the crude acetic acid in a fractionating column, thereby obtaining an acrylic acid purified product. This acrylic acid (purified product) is esterified in an esterification column, passes through an extracting column and a light-fraction separating column to obtain a crude acrylic ester, and a by-product (high-boiling fraction) is separated from the crude acrylic ester in a fractionating column, thereby obtaining an acrylic ester purified product.

Incidentally, in recent years, as the recovery of acrylic acid from the acrylic acid aqueous solution, an azeotropic separation method in which distillation is conducted using water and an azeotropic solvent, and an azeotrope of water and the azeotropic solvent is distilled away from the column top of an azeotropic separating column, whereas acrylic acid is recovered from the column bottom is also employed in place of the solvent extraction method using an extraction solvent.

In the case of the synthesis of methacrylic esters, a methacrylic ester purified product is obtained through the similar oxidation process and subsequent esterification process using isobutylene or t-butyl alcohol in place of the propylene.

Incidentally, as the method of the formation of a (meth)acrylic ester (an acrylic ester or a methacrylic ester), a method in which a (meth)acrylic ester of a lower alcohol and a higher alcohol are subjected to transesterification in the presence of a catalyst such as an acid, to produce a (meth)acrylic ester of a higher alcohol is also employed. The crude (meth)acrylic ester obtained by this transesterification is converted into a purified (meth)acrylic ester through catalyst separation, concentration, fractionation, and other steps.

A fraction separated upon distillation and purification of the foregoing crude acrylic ester or crude methacrylic ester contains a useful by-product such as a Michael adduct. Accordingly, the by-product is decomposed, and (meth)acrylic acid or an ester thereof, the starting alcohol, etc. are recovered As the decomposition method of a Michael adduct of an acrylic ester, a method of decomposition upon heating in the presence of a Lewis acid or a Lewis base is employed (see JP-A-49-55614 and JP-A-9-110791).

In the method of decomposing a Michael addition reaction product formed by a by-product in the production step of a (meth)acrylic ester using a Lewis acid or a Lewis base as a catalyst and recovering (meth)acrylic acid, (meth)acrylic ester and alcohol, in the case where the alcohol residue of the ester is branched, an olefin was formed as a by-product at the time of decomposition reaction and became an obstacle in operation. That is, since the olefin generated in this reaction generally has a low boiling point and is hardly condensed in a decomposition reactor or a condenser, there were encountered such problems that it obstructs an adequate operation of a vacuum reactor or distillation column and that it adversely affects the reaction results or separation ability.

The problems caused by the formation of an olefin as a by-product will be described below in detail with respect to the time of production of isobutyl acrylate and the time of production of 2-ethylhexyl acrylate.

In the decomposition step of a Michael adduct at the time of production of isobutyl acrylate, isobutylene derived from isobutyl alcohol is formed as a by-product as an olefin. This by-product isobutylene has an extremely low standard boiling point as 266.1 K so that it is hardly condensed in the decomposition reactor itself to be operated in the vacuum system or a condenser of a distillation column as a destination for recovery. For that reason, if the amount of isobutylene formed as a by-product increases, the control of the vacuum system is obstructed so that the decomposition reaction or distillation under an adequate pressure condition becomes difficult, and finally, the reaction or separation operation is adversely affected.

In the decomposition step of a Michael adduct at the time of production of 2-ethylhexyl acrylate, 2-ethyl-1-hexene derived from 2-ethylhexyl alcohol and an isomer thereof are formed as by-products. In the case where a fraction containing these olefins having 8 carbon atoms are recovered into the reaction system, not only these olefins cause azeotropy with water, but also they form an azeotrope together with the starting acrylic acid, resulting a serious problem of losing acrylic acid. In general, there are the case where the esterification is carried out in a reaction distillation mode in which the equilibrium of the reaction is shifted upon removal of water formed during the reaction from the system, thereby obtaining a high conversion and the case where after the reaction, the unreacted acrylic acid, water, alcohol, and acrylic ester are separated by extraction or distillation. In any of these modes, acrylic acid is dissolved in the aqueous phase of the column top fraction and lost.

Even in the case where the acrylic acid, 2-ethylhexyl alcohol and 2-ethylhexyl acrylate containing olefins recovered in the decomposition step of a Michael adduct are recovered in the purification system, a loss of acrylic acid is similarly caused in the distillation system of the purification system. Assuming that these materials are recovered into the distillation system free from acrylic acid or water, they are ultimately recycled into the reaction system together with light fractions such as 2-ethylhexyl alcohol, whereby the foregoing loss of acrylic acid is caused.

An object of the invention is to dissolve the foregoing problems of the background art and to provide a method of decomposing a by-products such as a Michael addition reaction product formed in the production step of a (meth)acrylic ester using an alcohol bearing a branched chain and having 3 or more carbon atoms, thereby recovering (meth) acrylic acid, (meth)acrylic ester, alcohol and the like, in which an olefin formed as a by-product can be decomposed at a high recovery while suppressing the formation thereof as the by-product.

DISCLOSURE OF THE INVENTION

The decomposition method of by-products at the time of production of a (meth)acrylic ester according to the invention is a method of thermally decomposing a by-product at the time of production of a (meth)acrylic ester using an alcohol bearing a branched chain and having 3 or more carbon atoms, which is characterized in that the decomposition reaction is carried out in the absence of a catalyst.

In the decomposition step of a Michael adduct formed as a by-product in the production step of a (meth)acrylic ester, an acid catalyst has hitherto been used for increasing the recovery. However, when an alcohol bearing a branched chain is used as the alcohol, the unreacted alcohol causes dehydration reaction by the action of the catalyst, to form an olefin. This olefin brought an evil of obstructing the control of the vacuum system as described previously.

As a result of researches made by the present inventor, it has been found that when an acid catalyst is not used, the formation of an olefin is rather suppressed, thereby improving the productivity.

The invention is made based on such finding. According to the invention, it is possible to efficiently decompose a Michael adduct formed as a by-product at the time of production of a (meth)acrylic ester using an alcohol bearing a branched chain and having 3 or more carbon atoms.

BEST MODE FOR CARRYING OUT THE INVENTION

Figure 1:
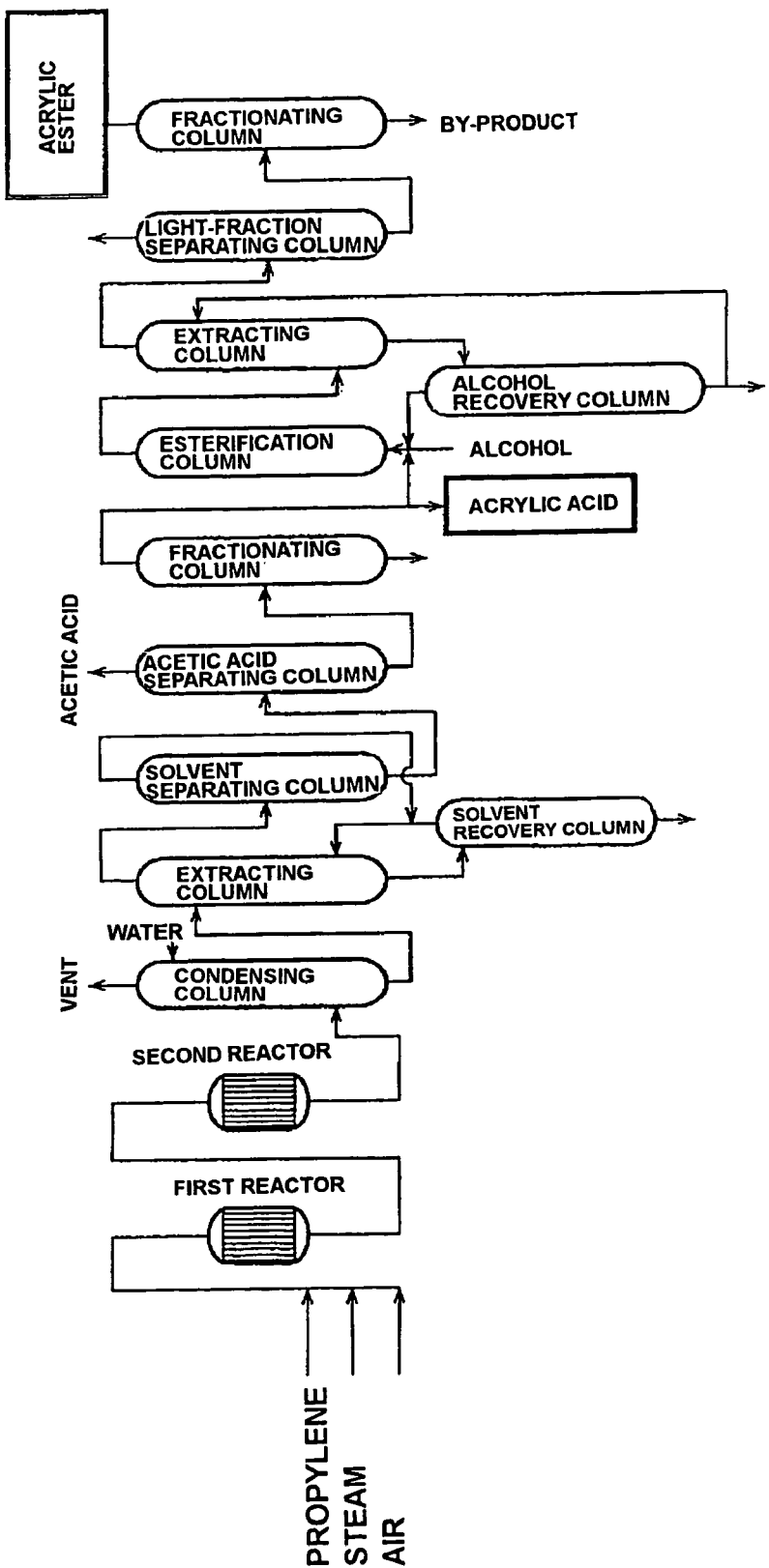
FIG. 1 shows one embodiment of a step flow of the production of acrylic acid and acrylic ester.

The invention will be described below in more detail.

As the (meth)acrylic ester of the invention, isobutyl (meth)acrylate, 2-ethylhexyl (meth)acrylate, isooctyl (meth) acrylate, isononyl (meth)acrylate, isodecyl (meth)acrylate, etc., each of which is produced from an alcohol bearing a branched chain and having 3 or more carbon atoms, and preferably 4 or more carbon atoms, such as isobutyl alcohol, 2-ethylhexyl alcohol, isooctyl alcohol, isononyl alcohol, and isodecyl alcohol, are preferable.

The Michael adduct is a by-product formed in the reaction step or purification step in the case of producing a (meth) acrylic ester and is a compound having a (meth)acryloyl group present in the production step and having been subjected to Michael addition with (meth)acrylic acid or an alcohol, or water. Examples of compounds having a (meth) acryloyl group present in the production step include carboxylic acids [such as (meth)acrylic acid; β-acryloxypropionic acid or β-meth-acryloxyisobutyric acid (hereinafter referred to as "dimer"), in which (meth)acrylic acid is subjected to Michael addition with (meth)acrylic acid; and a (meth)acrylic acid trimer (hereinafter referred to as "trimer") or a (meth)acrylic acid tetramer (hereinafter referred to as "tetramer"), in which the dimer is further subjected to Michael addition with (meth)acrylic acid] and corresponding (meth)acrylic esters in which such a carboxylic acid bearing a (meth)acryloyl group is esterified with the foregoing alcohol.

Specific examples of Michael adducts include β-acryloxypropionic acid or β-methacryloxyisobutyric acid or esters thereof β-alkoxypropionic acids or β-alkoxyisobutyric acids or esters thereof; β-hydroxypropionic acid or β-hydroxyisobutyric acid or esters or aldehydes thereof; dimers, trimers, tetramers or esters thereof; and β-acryloxy bodies, β-alkoxy bodies or β-hydroxy bodies thereof.

In the invention, the (meth)acrylic acid for producing a (meth)acrylic ester is preferably one obtained by catalytic vapor phase oxidation reaction of propane, propylene, acrolein, isobutylene, t-butyl alcohol, or the like. A gaseous oxidation reaction product is rapidly cooled and quenched with water. Thereafter, acrylic acid is separated from water by the azeotropic distillation method using an azeotropic solvent or the extraction method using a solvent; low-boiling compounds such as acetic acid are further separated; and a heavy fraction such as the Michael adduct is then separated, thereby producing high-purity (meth)acrylic acid. Incidentally, water and acetic acid may be separated at the same time using an azeotropic agent.

In the invention, as the method of producing a (meth) acrylic ester, a method of esterifying (meth)acrylic acid with an alcohol; and a method of subjecting an acrylic ester of a lower alcohol and an alcohol bearing a branched chain and having 3 or more carbon atoms to transesterification to produce an acrylic ester of the alcohol may be employed. Also, the production process can be conducted batchwise or continuously. Acid catalysts are generally used as a catalyst for the esterification or transesterification.

The production process of a (meth)acrylic ester preferably comprises a reaction step and a purification step in which washing, extraction, evaporation, distillation, etc. are carried out for the sake of conducting catalyst separation, concentration, purification, etc. of the crude acrylic ester liquid obtained in the reaction step. In the reaction step, the molar ratio of the starting materials, i.e., the (meth)acrylic acid or (meth)acrylic ester to the alcohol, the kind and amount of the catalyst to be used in the reaction, the reaction mode, the reaction condition, and the like are properly chosen depending upon the kind of the starting alcohol to be used. The Michael adduct formed as a by-product mainly in the esterification step is concentrated as a heavy fraction in the column bottom of a distillation column for recovering active components.

In the invention, in the reaction process for carrying out the decomposition reaction of the Michael adduct, though any mode of a continuous mode, a batch mode, a semi-batch mode, an intermittent extraction mode, or the like can be employed, a continuous mode is preferable. The form of a reactor is not particularly limited, but any form of a flow type tubular reactor, a thin film falling type reactor, a complete mixing vessel type agitation vessel reactor, a circulation type complete mixing vessel reactor, or the like can be employed. Any of a method in which active components contained in the decomposition reaction product are obtained by means of evaporation or distillation during the reaction or a method in which after the decomposition reaction, the active components are obtained by means of evaporation or distillation can be employed, but for the sake of obtaining a high recovery, the former reaction distillation mode is preferable.

In the case where the reaction distillation mode is employed, the reaction pressure largely relies on the reaction temperature described later, and a pressure under which the major part of the active components formed by the decomposition reaction and contained in the decomposition reaction starting material, such as acrylic acid, acrylic ester, and alcohol is employed.

In the invention, this decomposition is carried out in the absence of a catalyst.

The decomposition reaction temperature is preferably from 180 to 280° C., and especially preferably from 200 to 250° C. The liquid residence time on a basis of the extracted liquid is preferably from 0.5 to 20 hours, and especially preferably from 1 to 10 hours. Incidentally, in the case where the decomposition reaction is carried out by means of continuous reaction, the liquid residence time calculated based on the extracted liquid can be regarded as the reaction time. For example, in the case where the liquid volume in a reactor is 500 L, and the amount of the extracted liquid is 100 L/H, the residence time is 5 hours.

EXAMPLES

The invention will be described below in detail with reference to the following Examples and Comparative Examples.

Example 1

Decomposition reaction of a column bottom liquid of a product column in the production step of 2-ethylhexyl acrylate was carried out. The column bottom liquid had a formulation consisting of 22% by weight of 2-ethylhexyl acrylate, 48% by weight of 2-ethylhexyl β-2-ethylhexoxypropionate, 9% by weight of 2-ethylhexyl β-acryloxypropionate, 3% by weight of 2-ethylhexyl β-hydroxypropionate, and 18% by weight of other heavy materials and was fed at 3.0 kg/h into a decomposition reactor. The decomposition reactor had an inner diameter of 200 mm and a length of 400 mm and was made of Hastelloy C. A distillation column having an inter diameter of 30 mm and a length of 1,000 mm and charged with 500 mm of a coil pack and appending condenser and vacuum system were placed in the upper portion thereof. In the decomposition reactor, the reaction temperature was controlled by an external heater, and the liquid residence time was controlled by a liquid level in the decomposition reactor. The decomposition reaction was carried out under a reaction pressure of 80 kPa at a decomposition temperature of 230° C. for a residence time of 2 hours. As a result, a reaction residue consisting of 6% by weight of 2-ethylhexyl acrylate, 44% by weight of 2-ethylhexyl β-2-ethylhexoxypropionate, 9% by weight of 2-ethylhexyl β-acryloxypropionate, 2% by weight of 2-ethylhexyl β-hydroxypropionate, and 39% by weight of other heavy materials was obtained at 1.3 kg/h from the column bottom. A fraction containing acrylic acid, 2-ethylhexyl acrylate and 2-ethylhexyl alcohol as the major components was recovered at 1.70 kg/h from the column top and contained 0.15% by weight in total of 2-ethyl-1-hexene and its isomer.

Comparative Example 1

A decomposition reaction experiment was carried out using a starting material and device exactly the same as in Example 1. The starting material was fed at 3.0 kg/h, and p-toluenesulfonic acid was fed at 150 g/h as a catalyst. The decomposition reaction was carried out under a reaction pressure of 27 kPa at a decomposition temperature of 190° C. for a residence time of 2 hours. As a result, a reaction residue consisting of 5% by weight of 2-ethylhexyl acrylate, 42% by weight of 2-ethylhexyl β-2-ethylhexoxypropionate, 8% by weight of 2-ethylhexyl β-acryloxypropionate, 2% by weight of 2-ethylhexyl β-hydroxypropionate, 10% by weight of p-toluenesulfonic acid, and 33% by weight of other heavy materials was obtained at 1.5 kg/h from the column bottom. A fraction containing acrylic acid, 2-ethylhexyl acrylate and 2-ethylhexyl alcohol as the major components was obtained at 1.65 kg/h from the column top of the distillation column in the upper portion of the decomposition reactor and contained 2.78% by weight in total of 2-ethyl-1-hexene and its isomer.

Example 2

Decomposition reaction was carried out at the same temperature for the same liquid residence time as in Example 1, using the decomposition reaction device as in Example 1 and using a column bottom liquid of a heavy-fraction separating column in the production plant of isobutyl acrylate. The column bottom liquid as the starting material had a formulation consisting of 19% by weight of isobutyl acrylate, 65% by weight of isobutyl β-isobutoxypropionate, 4% by weight of isobutyl β-acryloxypropionate, 2% by weight of isobutyl β-hydroxypropionate, and 10% by weight of other heavy materials and was fed at 3.0 kg/h. The decomposition was carried out under a pressure of 100 kPa. A recovered liquid was obtained at 1.85 kg/h from the column top of the distillation column in the upper portion of the decomposition reactor. The total amount of isobutylene in the recovered liquid and collected in an acetone-dry ice trap was 2.7 g/h.

Comparative Example 2

The same decomposition reaction device as in Example 1 was used, and the same column bottom liquid as in Example 2 was fed at 3.0 kg/h as the starting material. Decomposition was carried out at a temperature of 190° C. under a pressure of 40 kPa for the same liquid residence time as in Example 2, while feeding p-toluenesulfonic acid at 150 g/h. A recovered liquid was obtained at 1.79 kg/h from the column top of the distillation column in the upper portion of the decomposition reactor. The total amount of isobutylene in the recovered liquid and collected in an acetone-dry ice trap was 48 g/h.

While the invention has been described in detail and with reference to specific embodiments thereof, it will be apparent to one skilled in the art that various changes and modifications can be made therein without departing from the spirit and scope thereof.

This application is based on a Japanese patent application filed Dec. 26, 2001 (Japanese Patent Application No. 2001-

394447), the contents of which are incorporated therein and made hereof by reference.

INDUSTRIAL APPLICABILITY

As described previously, according to the invention, decomposition treatment of a Michael addition reaction product formed as a by-product in the production step of a (meth)acrylic ester using an alcohol bearing a branched chain and having 3 or more carbon atoms is carried out, whereby (meth)acrylic acid, (meth)acrylic ester and alcohol can be recovered with high efficiency while suppressing the formation of an olefin as a by-product.

The invention claimed is:

1. A method comprising:
    decomposing a by-product produced during production of a (meth)acrylic ester by a process which uses an alcohol bearing a branched chain and which has 3 or more carbon atoms, comprising:
    thermally decomposing said by-product in the absence of a Lewis acid or base catalyst;
    wherein the by-product at the time of production of a (meth)acrylic ester contains a Michael adduct of a branched chain alcohol.

2. The method of claim 1, wherein the by-product at the time of production of a (meth)acrylic ester is a column bottom liquid of a distillation column for separating a high-boiling material in the production step of a (meth)acrylic ester.

3. The method of claim 1,
    wherein the by-product is formed by esterification of (meth)acrylic acid and a branched chain alcohol or transesterification of a (meth)acrylic ester and a branched chain alcohol.

4. The method of claim 3, wherein the branched chain alcohol is isobutyl alcohol, 2-ethylhexyl alcohol, isooctyl alcohol, isononyl alcohol, or isodecyl alcohol.

5. The method of claim 1, wherein the Michael adduct is a compound in which water, an alcohol, or (meth)acrylic acid is added to the α-position or β-position of a (meth)acryloyl group.

6. The method of claim 1, wherein the decomposition treatment temperature is from 180 to 280° C.

7. The method of claim 1, wherein the decomposition treatment temperature ranges from 200 to 250° C.

8. The method of claim 1, wherein the decomposition treatment time is from 0.5 to 20 hours.

9. The method of claim 1, wherein the decomposition treatment time is from 1 to 10 hours.

10. The method of claim 1, wherein said process uses an alcohol bearing a branched chain and which has 4 or more carbon atoms.

11. The method of claim 1, wherein said by-product is produced during production of an acrylic ester.

12. The method of claim 1, wherein said by-product is produced during production of a methacrylic ester.

* * * * *